(12) United States Patent
Sabbah et al.

(10) Patent No.: US 9,452,458 B2
(45) Date of Patent: Sep. 27, 2016

(54) COMPOSITIONS OF MATTER AND USES THEREOF IN THE TREATMENT OF WASTE MATERIALS

(75) Inventors: Isam Sabbah, Shfaram (IL); Nedal Massalha, Daboria (IL); Ahlam Saliba, Shfaram (IL)

(73) Assignee: AgRobics, Ltd., Shefar-Am (IL)

( * ) Notice: Subject to any disclaimer, the term of this patent is extended or adjusted under 35 U.S.C. 154(b) by 0 days.

(21) Appl. No.: 13/636,657

(22) PCT Filed: Mar. 17, 2011

(86) PCT No.: PCT/IL2011/000263
§ 371 (c)(1),
(2), (4) Date: Sep. 21, 2012

(87) PCT Pub. No.: WO2011/117864
PCT Pub. Date: Sep. 29, 2011

(65) Prior Publication Data
US 2013/0005013 A1    Jan. 3, 2013

Related U.S. Application Data

(60) Provisional application No. 61/317,444, filed on Mar. 25, 2010.

(51) Int. Cl.
| | | |
|---|---|---|
| B09B 1/00 | (2006.01) | |
| B09C 1/00 | (2006.01) | |
| B09C 1/10 | (2006.01) | |
| C02F 3/10 | (2006.01) | |
| C02F 3/28 | (2006.01) | |
| C12N 1/20 | (2006.01) | |
| C12N 1/38 | (2006.01) | |
| C12N 11/08 | (2006.01) | |
| C12P 5/02 | (2006.01) | |
| B09B 3/00 | (2006.01) | |
| C12M 1/12 | (2006.01) | |
| C02F 103/26 | (2006.01) | |
| C02F 103/32 | (2006.01) | |
| C02F 103/34 | (2006.01) | |
| C02F 103/36 | (2006.01) | |

(52) U.S. Cl.
CPC ............. *B09B 3/00* (2013.01); *B09C 1/002* (2013.01); *B09C 1/10* (2013.01); *C02F 3/104* (2013.01); *C02F 3/106* (2013.01); *C02F 3/108* (2013.01); *C02F 3/2806* (2013.01); *C02F 3/2846* (2013.01); *C12M 25/14* (2013.01); *C12N 1/20* (2013.01); *C12N 1/38* (2013.01); *C12N 11/08* (2013.01); *C12P 5/023* (2013.01); *C02F 2103/26* (2013.01); *C02F 2103/32* (2013.01); *C02F 2103/325* (2013.01); *C02F 2103/327* (2013.01); *C02F 2103/343* (2013.01); *C02F 2103/365* (2013.01); *C02F 2303/10* (2013.01); *Y02E 50/343* (2013.01); *Y02W 10/15* (2015.05); *Y02W 10/30* (2015.05)

(58) Field of Classification Search
None
See application file for complete search history.

(56) References Cited

U.S. PATENT DOCUMENTS

| | | |
|---|---|---|
| 3,861,993 A | 1/1975 | Guthrie |
| 3,889,417 A | 6/1975 | Wood et al. |
| 4,983,299 A | 1/1991 | Lupton et al. |
| 5,217,616 A | 6/1993 | Sanyal et al. |
| 6,143,692 A | 11/2000 | Sanjay et al. |
| 6,258,589 B1 | 7/2001 | Dybas et al. |

FOREIGN PATENT DOCUMENTS

| | | |
|---|---|---|
| JP | 2003-235554 A | 8/2003 |
| WO | WO-2004024356 A1 | 3/2004 |
| WO | WO-2011123850 A2 | 10/2011 |

OTHER PUBLICATIONS

Morgan CA et al. Preservation of microorganisms by drying; A review. 2006. Journal of Microbiological Methods. 66. pp. 183-193.*
Tatsuo S. Machine translation of JP2003235554 published on Aug. 26, 2003. p. 1-7.*
Gavrilescu M. Engineering concerns and new developments in anaerobic waste-water treatment. 2002. Clean Techn. Environ. Policy. 3:346-362.*
Borja, R., Alba, J., and Banks, C.J., 1997: Impact of the main phenolic compounds of olive mill wastewater (OMW) on the kinetics of acetoclastic methanogenesis. *Process Biochem.*, 32:121-133.
Erguder, T.H. et al., "Anaerobic treatment of olive mill wastes in batch reactors", *Process Biochem*, 36: 243-248, 2000.
Ethaliotis, C.; Papadopoulou, K.; Kotsou, M.; Mari, I.; Balis, C., 1999: "Adaptation and population dynamics of Aztobacter vinelandii during aerobic biological treatment of olive mill wastewater", in: *FEMS Microbiol. Ecol.*, 30: 301-311.
Han Wei, et al., "Biohydrogen production with anaerobic sludge immobilized by granular activated carbon in a continuous stirred-tank", *Journal of Forestry Research*, 21(4), 509-513, 2010.
International Search Report issued in counterpart International Application No. PCT/IL2011/000263 dated Feb. 14, 2012.
Lovley, et al., 1996: "Humic substances as electron acceptors for microbial respiration". *Nature* 382, 445-448.
Niaounakis, N. and Halvadakis, C.P., 2004: "Olive Mill waste management—Literature review and patent survey". NAIAS, Typothito-George Dardanos Publications, Athens.

(Continued)

*Primary Examiner* — Paul Holland
(74) *Attorney, Agent, or Firm* — Venable LLP; Michele V. Frank

(57) ABSTRACT

Disclosed are compositions of matter comprising at least one anaerobic degrading microorganism, particulate active carbon and a polymeric solid support wherein the anaerobic degrading microorganism and particulate active carbon are entrapped in the polymeric support and processes for preparing the same. The disclosed compositions of matter are used in processes of anaerobic degradation of waste materials resulting in high yields of biogas production.

10 Claims, 11 Drawing Sheets

(56) References Cited

OTHER PUBLICATIONS

Ramos, Ana C.T. et al., "Mass transfer improvement of a fixed-bed anaerobic sequencing batch reactor with liquid-phase circulation", INCI v. 28 n.4 Caracas Abr., 2003.

Sabbah, I. et al., "The effect of pretreatment on anaerobic activity of olive mill wastewater using batch and continuous systems," *Process Biochem*, 39: 1947-1951, 2004.

Schwarzenbach, et al., 1990: "Quinone and iron porphyrin mediated reduction of nitroaromatic compounds in homogeneous aqueous solution". *Environ. Sci. Technol.* 24:1566-1574.

Seghezzo, L. et al., "A review: The Anaerobic Treatment of Sewage in USAB and EGSB Reactors", *Bioresource Technol.* 65: 175-190, 1998.

Varesche, M. et al., "Microbial colonization of polyurethane foam matrices in horizontal-flow anaerobic immobilized-sludge reactor", *Appl. Microbiol Biotechnol* 48, 534-538, 1997.

Varesche, M. et al., "Characterization of anaerobic biomass immobilized in polyurethane foam matrices from HAIS reactor by scanning electron microscopy", Universidade de São Paulo, 1996.

Hwu, C.-S. et al. "Screening of immobilization materials for anaerobic wastewater treatment", *Immob. Cells: Basics and Applications*; p. 98-106, 1996.

Written Opinion from the International Searching Authority issued in counterpart International Application No. PCT/IL2011/000263 dated Feb. 14, 2012.

Zaiat, M. et al., "Cell Wash-Out and External Mass Transfer Resistance in Horizontal-Flow Anaerobic Immobilized Sludge Reactor"; *Wat. Res* 30, 2435-2439, 1996.

Zeeman, G. et al., "Anaerobic Treatment of Complex Wastewater and Waste Activated Sludge-Application of an Upflow Anaerobic Solid Removal and Pre-Hydrolysis of Suspended Cod", *Water Sci. Technol.*, 35, 121-128, 1997.

* cited by examiner

COMPOSITIONS OF MATTER AND USES THEREOF IN THE TREATMENT OF WASTE MATERIALS

FIELD OF THE INVENTION

This invention relates to compositions of matter for treating waste materials and to processes for treating waste materials as well as the production of biogas from waste materials.

BACKGROUND OF THE INVENTION

The use of industrialized agricultural technologies has expanded and grown significantly, concomitant with world population growth and the growing need for nourishment. The processing and manufacturing of mass quantities of agricultural products and crops, such as for example vegetables, fruits, meat, and diary products, results in large amounts of wastes, especially in the form of strong refractory wastewater produced in such industries. The disposal of such wastes in environmentally unsuitable and unsafe forms has caused severe ecological problems. For example, wastewater from olive mills, paper mills, meat industry, dairy industry and so forth contain very high organic load and high content of microbial growth-inhibiting compounds.

Current agro-industrial wastewater treatment technologies are based on biological (mainly anaerobic) and physico-chemical treatment systems, in which some of the effluents are disposed without any treatment. The anaerobic treatment systems involve unstable long and slow processes characterized by long start-up periods.

Although agricultural waste is considered as source of groundwater, air, landscape and nature pollution, it could be converted into environmentally and economically profitable products. The high organic matter concentration found in agricultural waste may serve as a source for biogas production under anaerobic digestion conditions.

A variety of anaerobic digestion technologies are available [Seghezzo L. et al., *Bioresource Technol.* 65: 175-190, 1998; Zemman, G. et al., *Water Sci. Technol.*, 35, 121-128, 1997]. However, the anaerobic digestion processes currently used are known of their low methane gas production yields, process instability, high retention time and long start-up period.

Within the different anaerobic treatment systems studied so far, up-flow anaerobic sludge blanket (UASB) reactor is considered to be one of the most popular bioreactors to treat agro-industrial wastewaters characterized by high organic load and high efficiency of Chemical Oxygen Demand (COD) [Erguder, T. H. et al., *Process Biochem*, 36: 243-248, 2000]. However, the major problems involved with the UASB system are the required long-term start-up periods, instability of the biological activity, high toxicity of phenolic compounds and tannins, and the need to adjust the pH in the medium of the reactor [Sabbah, I. et al., *Process Biochem*, 39: 1947-1951, 2004].

Immobilization of anaerobic sludge for wastewater treatment is known in the art, however, so far limited research was conducted in the field of such immobilization [R. H. Wijffels, et al., Elsevier Science B.V. p. 98-106, 1996; M. Varesche et al., "Characterization of anaerobic biomass immobilized in polyurethane foam matrices from HAIS reactor by scanning electron microscopy", 1996; M. Varesche et al., Appl. Microbiol Biotechnol 48, 534-538, 1997; Han Wei et al., Journal of Forestry Research, 21, 509-513, 2010; M. Zaiat et al., Wat. Res 30, 2435-2439, 1996; Ana C. T. Ramos et al., "Mass transfer improvement of a fixed-bed anaerobic sequencing batch reactor with liquid-phase circulation", 2003]. In known immobilization processes solid matrices such as polyurethane (PU) foam matrices are immersed in anaerobic reactors and biomass can attach to the support matrix (polyurethane cube) and then growth of the biomass in the pores of the polyurethane foam occurs.

SUMMARY OF THE INVENTION

There is a long felt need to improve the performance of anaerobic digestion systems. Thus, the present invention aims to provide improved compositions of matter that are used in such systems.

The present invention generally relates to compositions of matter comprising anaerobic degrading microorganisms, particulate activated carbon (PAC), and optionally humic acid (HA). The compositions of matter according to the invention may be immobilized on a solid support such as a polymeric support.

The compositions of matter according to invention are used in processes of anaerobic degradation of waste materials resulting in production of biogas. Surprisingly, the compositions of matter according to the invention provide the processes with enhanced removal of organic pollution and high production of biogas.

The compositions of matter according to the invention are also used in anaerobic treatment systems (e.g., UASB system) and as such provide processes of anaerobic degradation with the advantage of increased stability, reduced HRT (hydraulic retention time) and start-up periods, reduced retention time periods as well as enhancement of the biogas production. The high yields of biogas production constitute a significant and economic benefit as an energy source.

Thus, in one aspect of the present invention there is provided a composition of matter comprising at least one anaerobic degrading microorganism, particulate active carbon and a polymeric solid support, wherein the anaerobic degrading microorganism and the particulate active carbon are entrapped or embedded in the polymeric support.

In another aspect of the present invention there is provided a composition of matter comprising at least one anaerobic degrading microorganism, particulate active carbon and an in-situ formed polymeric solid support, wherein the anaerobic degrading microorganism and the particulate active carbon are entrapped or embedded in the polymeric support.

In a further aspect of the present invention there is provided a process for the manufacture of a composition of matter comprising anaerobic degrading microorganisms, particulate activated carbon and a solid polymeric support, the process comprises:
(a) providing anaerobic degrading microorganisms;
(b) mixing the anaerobic degrading microorganisms with particulate activated carbon;
(c) adding to the mixture obtained is step (b) at least one pre-polymer capable of being polymerized to form a solid polymeric support; and
(d) allowing polymerization of the at least one pre-polymer to occur;
whereby the composition of matter wherein the anaerobic degrading microorganisms and the particulate active carbon are entrapped or embedded in the polymeric solid support is obtained.

In yet a further aspect of the present invention there is provided a process for the production of biogas from waste, the process comprises:
(a) providing a composition of matter according to the invention; and
(b) contacting the waste with the composition of matter under anaerobic conditions; thereby producing the biogas.

In an additional aspect of the present invention there is provided a use of a composition of matter according to the invention for the production of biogas from waste under anaerobic conditions.

In a further aspect of the present invention there is provided a composition of matter according to the invention for use in the production of biogas from waste under anaerobic conditions.

In yet an additional aspect of the present invention there is provided a use of a composition of matter according to the invention for treating waste water.

In a further aspect of the present invention there is provided a composition of matter according to the invention for use in the treatment of waste water.

BRIEF DESCRIPTION OF THE DRAWINGS

In order to understand the invention and to see how it may be carried out in practice, embodiments will now be described, by way of non-limiting example only, with reference to the accompanying drawings, in which:

FIG. 2A shows the biogas production profile observed with first used compositions of matter.

FIG. 2B shows the biogas production profile observed with recycled compositions of matter.

FIG. 3A shows the biogas production profile observed with buffered olive mill wastewater.

FIG. 3B shows the biogas production profile observed with non-buffered olive mill wastewater.

FIG. 4A shows SEM image of a composition of matter obtained with Poly 74-30 Clear B polymer.

FIG. 4B shows SEM image of a composition of matter obtained with HYPOL*2002 Pre-polymer.

FIG. 6A shows the biogas production profile observed with a composition of matter obtained with Poly 74-30 Clear B polymer.

FIG. 6B shows the biogas production profile observed with a composition of matter obtained with HYPOL*2002 Pre-polymer.

ABBREVIATIONS

Figure 1:
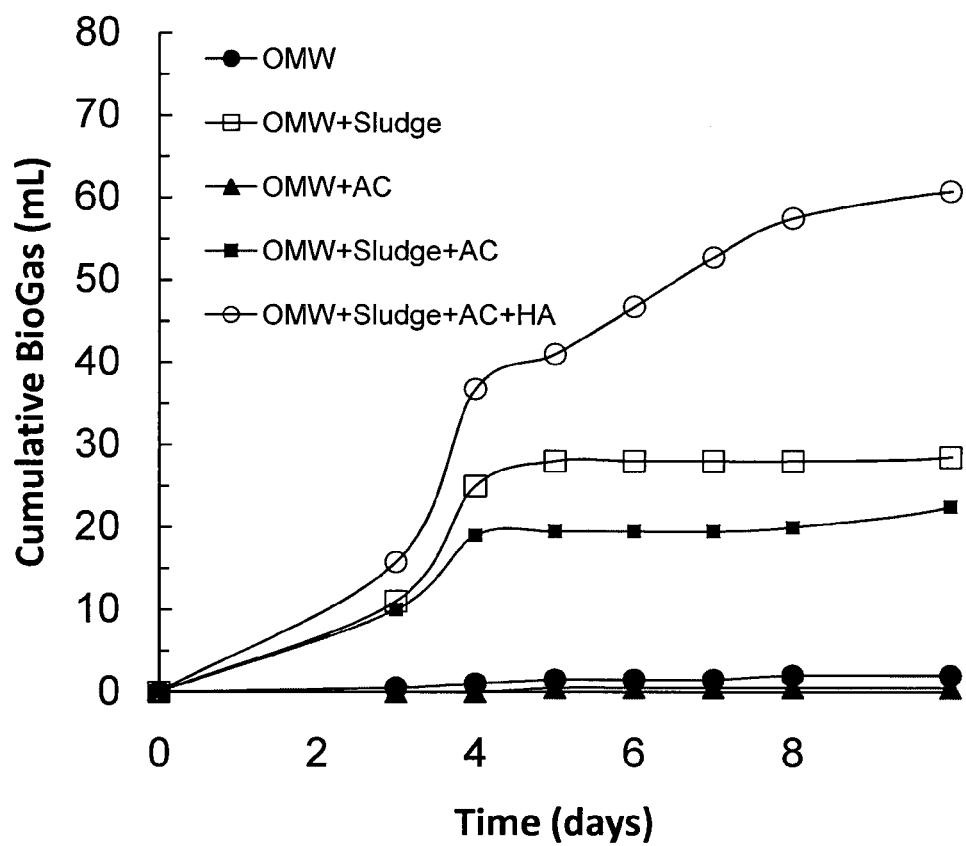
FIG. 1 shows the biogas production profile observed with various compositions of matter according to the invention.

The following abbreviations are used herein:
AC Active carbon, activated carbon
AD Anaerobic digester
BOD Biochemical Oxygen Demand
COD Chemical Oxygen Demand
DOM Dissolved organic matter
EC Electrical conductivity
EGSB Extended granular sludge bead
GAC Granulated active carbon
HA Humic acid
HRT Hydraulic retention time
HS Humic substances
OMW Olive mill wastewater
PAC Powdered active carbon
PU Polyurethane
TKN Total Kjeldahl Nitrogen
TSS Total suspended solids
TS Total solids
UASB Up flow anaerobic sludge blanket
UASR Up flow anaerobic solid removal
VFA Volatile fatty acids
VSS Volatile suspended solids
VS Volatile solids

DETAILED DESCRIPTION OF EMBODIMENTS

The present invention provides compositions of matter comprising anaerobic degrading microorganism (biomass), particulate active carbon and a polymeric solid support wherein the biomass and the particulate active carbon are entrapped or embedded in the polymeric support. The compositions of matter according to invention may further comprise humic acid. The compositions of matter according to invention are used in processes of anaerobic degradation of waste materials resulting in high yields of biogas production. The compositions of matter according to the invention are used in anaerobic process for biodegradation of organic content found in waste materials with significantly high efficiency of organic mass removal and high biogas production yields.

Thus, according to one aspect of the present invention, there is provided a composition of matter comprising at least one anaerobic degrading microorganism, particulate active carbon and a polymeric solid support, wherein the anaerobic degrading microorganism and the particulate active carbon are entrapped or embedded in the polymeric support.

The composition of matter according to the invention may be of various forms (e.g., beads, films, powders, granules, foams) or shapes (e.g., cubes, spheres).

In some embodiments the solid support may be in a semi-solid (quasi-solid) state e.g., foam, emulsion or gel.

In some embodiments the composition of matter of the invention may be porous.

According to another aspect of the present invention, there is provided a composition of matter comprising at least one anaerobic degrading microorganism, particulate active carbon and an in-situ formed polymeric solid support, wherein the anaerobic degrading microorganism and the particulate active carbon are entrapped or embedded in the polymeric support.

Thus, in some embodiments the polymeric support is formed in-situ in the presence of other ingredients of the compositions of matter e.g., anaerobic degrading microorganisms (biomass), which may be dried, activated carbon, etc, to achieve entrapment, embedding or integration of at least one of these other ingredients of the composition of matter according to the invention in the resulting polymeric support.

In some embodiments the polymeric support is a homo-polymeric or a co-polymeric support. In some further embodiments the polymeric support is a polyurethane (PU, a polymer possessing a polyurethane bond). The preparation of such polymers has been previously disclosed in U.S. Pat. No. 3,861,993 to Guthrie and U.S. Pat. No. 3,889,417 to Wood et al., these patents are fully incorporated herein by reference. In some embodiments the polymer (e.g., polyurethane) is hydrophilic. In some further embodiments the polymer (e.g., polyurethane) is hydrophobic. In yet further embodiments the polymer is formed from pre-polymer units which may be hydrophobic (e.g., provided in oil solution) or hydrophilic (e.g., provided in an aqueous solution).

In some embodiments the composition of matter according to the invention may have a specific density of about 1 g/cm$^3$ and below (e.g., 0.95, 0.85, 0.80, 0.75, 0.70, 0.65. 0.60, 0.55, 0.50, 0.45, 0.40, 0.35, 0.30, 0.25, 0.20, 0.15 and 0.10 g/cm$^3$). In some embodiments the specific density is 0.9 g/cm$^3$. Low specific densities of the compositions according to the invention provide the compositions with an inherent floating capability which may be advantageous when such compositions are used in the processes of the invention as will be illustrated herein below.

In some embodiments the composition of matter according to the invention is non-biodegradable e.g., the composition may have a long shelf life and/or may be efficiently used in the processes according to the invention for a long period of time and/or in multiple cycles of operation without being degraded. Typically, the compositions of matter according to the invention may be used for example in a process for the production of biogas (as disclosed herein below) and/or for the treatment of waste water for at least 10 days e.g., 10 days, 20 days, 50 days and/or with passing relatively large volumes of for example waste water through the systems used without affecting the stability and/or efficiency of the compositions of matter of the invention.

In some embodiments the composition of matter of the invention may optionally further comprise HA. In some embodiments the HA is entrapped or embedded in the polymeric support of the composition of matter. In some further embodiments the composition of matter is impregnated with HA. In further embodiments the HA is adsorbed onto AC. In yet further embodiments the AC is coated with HA and the biomass (anaerobic degrading microorganisms) and the coated AC are entrapped or embedded in the polymeric support.

The HA according to the invention may be in its monomeric or polymeric form. In some embodiments the HA is cross linked. In some further embodiments the molecular weight of the HA ranges from about 800 Daltons to about 500,000 Daltons. In some embodiments the average molecular weight of HA is about 5000 Daltons. In other embodiments the average molecular weight is about 50,000 Daltons.

As used herein above and below the term "about" refers to ±10% of the indicated value.

In some embodiments the anaerobic degrading microorganisms constitute from more than zero and up to about 30% of the total weight of the composition of matter. In some embodiments the anaerobic degrading microorganisms constitute about 5%, 10%, 15%, 20%, 25% or 30% of the total weight of the composition of matter. In yet further embodiments the anaerobic degrading microorganisms constitute about 21.6% of the total weight of the composition of matter.

In some embodiments the weight ratio between the AC and the total weight of the composition of matter ranges from above zero to about 1, e.g., 0.01, 0.02, 0.03, 0.04, 0.05, 0.06, 0.07, 0.08, 0.09, 0.1, 0.2 and so on. In some embodiments the ratio is 0.02.

In some further embodiments the weight ratio between the AC and the biomass ranges from between about 0.05 to about 1. In some embodiments the ratio is 0.07. It is noted that this ratio is given provided that the biomass is dry (in some embodiments ratio of 0.07 with dry biomass equals a ratio of 0.44 when the biomass is provided wet).

In some embodiments the weight ratio between the AC and the polymeric support ranges from between above zero to about 1, e.g., 0.01, 0.02, 0.03, 0.04, 0.05, 0.06, 0.07, 0.08, 0.09, 0.1, 0.2, and so on. In some embodiments the ratio is 0.07.

In some embodiments the weight ratio between the biomass and the polymeric support is more than zero and up to about 1 e.g., 0.1, 0.2, 0.3, 0.4, 0.5, 0.6, 0.7, 0.8, 0.9. In some embodiment the ratio is 0.9. It is noted that this ratio is given provided that the biomass is dry (in some embodiments ratio of 0.9 with dry biomass equals a ratio of 1.5 when the biomass is provided wet).

In another aspect of the present invention, there is provided a composition of matter comprising at least one anaerobic degrading microorganism and humic acid, wherein said humic acid is adsorbed onto particulate active carbon.

In some embodiments the humic acid in the composition of matter according to the invention is adsorbed onto particulate activated carbon. As used herein the terms "adsorbed", "fixed", "affixed" "adhered" or any lingual variation thereof are used interchangeably and refer to accumulation of the HA on the surface of the particulate activated carbon. Adsorption may be via physical interaction or via chemical interactions or a combination of the same. The terms "coated" or "covered" or any lingual variation thereof are used interchangeably and refer to a particulate active carbon onto which HA is adsorbed.

As used herein, the terms "activated carbon", "activated charcoal" and "activated coal" or any lingual variations thereof are interchangeable and refer to a porous carbon with a large surface area for example 500 m$^2$/g and above. In some embodiments the activated carbon is of a surface area of about 1000 m$^2$/g. At times the term "activated carbon" is used interchangeably with the term "activated carbon matrix".

Without wishing to be bound by any theory, the particulate activated carbon may serve as a matrix for the HA and microorganisms. Also, the high surface area of the activated carbon may provide it with high adsorption capacity and an increased amount of sites accessible to the biomass, resulting in increased performance of the anaerobic degradation in the process of the invention as will be illustrated herein below.

The activated carbon is made in particular form. Hence, the activated carbon according to the invention is particulate active carbon. In some embodiments the particulate active carbon is selected from powdered active carbon (PAC), granulated active carbon (GAC), extruded active carbon or any combination thereof. In further embodiments the particulate active carbon is impregnated carbon containing at least one inorganic impregnant, which may be of different types, such as iodine, silver and cations such as, but not limited to Al$^{+3}$, Mn$^{+2}$, Zn$^{+2}$, Fe, Li$^{+1}$ and Ca$^{+2}$ cations.

In some embodiments the composition of matter according to the invention may further comprise at least one inorganic material.

The inorganic material may be selected from a metal, a transition metal, metal oxide or transition metal oxide. In some embodiments, the inorganic material is an element of Groups IIIB, IVB, VB, VIIB, VIIB, VIIIB, IB, IIB, IIIA, IVA and VA of block d of the Periodic Table of the Elements.

In some embodiments, the inorganic material is a transition metal selected from Groups IIIB, IVB, VB, VIIB, VIIB, VIIIB, IB and IIB of the Periodic Table. In some embodiments, the transition metal is a metal selected from the group consisting of Sc, Ti, V, Cr, Mn, Fe, Ni, Cu, Zn, Y, Zr, Nb, Tc, Ru, Mo, Rh, W, Au, Pt, Pd, Ag, Mn, Co, Cd, Hf, Ta, Re, Os, Ir, Hg, Rf, Db, Sg, Bh, Hs, and Mt.

In some embodiments, the transition metal is selected from iron or nickel.

In some embodiments, the transition metal oxide is selected from the group consisting of FeO, $Fe_2O_3$ and $Fe_3O_4$.

The term "biomass" as used herein should be understood to encompass at least one anaerobic community of microorganisms. The microorganisms may originate from a waste/contamination source.

As used herein the terms "anaerobic community of microorganisms", "anaerobic degrading microorganisms", "anaerobic pollutant-degrading sludge" and "sludge" are interchangeable and refer to microorganisms capable of breaking down biodegradable material in the absence of oxygen. Non-limiting examples of such microorganisms are anaerobic communities of microorganisms of UASB systems e.g., a sludge characterized by total solids of 28.6% and volatile solids of 26%, which mean a ratio of VS/TS=0.91.

In some embodiments the anaerobic degrading microorganisms are selected from the group consisting eukaryotes, multicellular eukaryotes, eubacteria, sulfur-oxidizing bacteria, colorless sulfur bacteria, acidogenic bacteria, anaerobic bacteria, and methanogenic bacteria. Non-limiting examples of anaerobic bacteria are *Clostridium, Bifidobacterium, Desulphovibrio, Actinomyces*, and *Staphylococcus*. Non-limiting examples of methanogenic bacteria are *Methanobacterium, Methanobacillus, Methanococcus*, and *Methanosarcina*.

In some embodiments, the weight ratio between the HA and the particulate AC in the composition of matter according to the invention ranges from about 0.0017 to about 0.17. In some embodiments the ratio is 0.0017. In other embodiments the ratio is 0.017. In further embodiments the ratio is 0.17.

In some embodiments the weight ratio between the AC and the total weight of the composition of matter is 0.17. In some further embodiments the weight ratio between the HA and the total weight of composition of matter is 0.0025.

In some embodiments, the weight ratio between the particulate AC coated with HA and between the biomass ranges from between about 0.05 to about 1. In some embodiments the ratio is 0.05. In other embodiments the ratio is 1. It is noted that this ratio is given provided that the biomass is wet (in some embodiments the ratio of 0.05 for wet biomass is equivalent to a ratio of 0.17 for dry biomass).

As a person skilled in the art would realize the amounts and/or concentrations of biomass, AC and HA, as well as any other constituents, employed in the actual composition of matter according to the invention (e.g., polymeric support) may vary depending inter alia on the extent of biogas production sought to be achieved and any other utilization of the compositions. Therefore, any specific weight ratio between the constituents of the composition of matter of the invention e.g., the weight ratio between the HA and the particulate AC, weight ratio between the AC and the total weight of the composition of matter, weight ratio between the AC and the biomass, and weight ratio between the particulate AC coated with HA and the biomass provided herein should be taken to mean an approximate ratio. For example, the expression "about 0.0017" refers to a ratio which may be slightly below or slightly above or within the indicated range. For example, the range "from about 0.0017 to about 0.17" would mean 0.0011, 0.0012, 0.0013, 0.0014, 0.0015, 0.0016, 0.0017, 0.0018, 0.0019, 0.002 and so on to 0.02, 0.025, 0.03, 0.035, 0.04 and so on to 0.1, 0.11, 0.12, 0.13, 0.14, 0.15, 0.16, 0.17. Any equivalent ratios are within the scope of the present invention.

In some embodiments the composition of matter according to the invention is provided in a suspension form.

In further embodiments the composition of matter according to the invention may be immobilized on a solid support, such as a polymeric support. In yet further embodiments the polymeric support may constitute part of the composition of matter wherein at least one other ingredient comprised in the composition of matter is entrapped or embedded in the polymeric support. In some embodiments at least one of the ingredients is integrated in the polymeric support.

As used herein the terms "support", "matrix" or any lingual variation thereof are used interchangeably.

The immobilization of the composition of matter according to the invention on a solid support e.g., polymeric support, may be achieved by various techniques. In some embodiments immobilization may be via simultaneous entrapment or embedding of biomass, PAC and optionally HA in a polymeric support. In other embodiments AC and biomass may be first entrapped or embedded within a polymeric support followed by addition of HA resulting in a composition of matter which is impregnated with HA. In further embodiments AC is first coated with HA followed by addition of biomass and immobilization on a polymeric support. The order of the steps may be interchangeable.

Thus, according to another aspect of the present invention, there is provided a composition of matter comprising at least one anaerobic degrading microorganism, particulate active carbon and humic acid, wherein the composition is immobilized on, entrapped or embedded in a solid support.

The composition of matter according to the invention may be of various forms (e.g., beads, films, powders, granules, foams) or shapes (e.g., cubes, spheres).

As used herein, the term "immobilizing" or any lingual variations thereof is envisaged as binding, integrating, enclosing in, incorporating into, embedding, encapsulating or entrapment of the composition of matter of the invention or its constituents to, onto or within a solid support e.g., polymeric support. The immobilization of the composition of matter on the solid support may be via physical interactions, chemical interactions or combination of the same. The interaction may be one or more of solvation, dissolution, gelation, coordination, complexation, electrostatic interaction, hydrophobic interaction, hydrophilic interaction, acid-base, ionic, covalent, etc. In some embodiments immobilization may be via in-situ formation of a polymeric support in the presence of other ingredients of the compositions of matter e.g., biomass, which may be dried, activated carbon, etc, to achieve integration, entrapment or embedding of at least one of these other ingredients of the composition of matter according to the invention in the resulting polymeric support.

In another aspect of the present invention, there is provided a process for the manufacture of a composition of matter comprising anaerobic degrading microorganisms, particulate activated carbon and a solid polymeric support, the process comprises:

(a) providing anaerobic degrading microorganisms;
(b) mixing the anaerobic degrading microorganisms with particulate activated carbon;
(c) adding to the mixture obtained is step (b) at least one pre-polymer capable of being polymerized to form a solid polymeric support; and
(d) allowing polymerization of the at least one pre-polymer to occur;
whereby the composition of matter wherein the anaerobic degrading microorganisms and the particulate active carbon are entrapped or embedded in the polymeric solid support is obtained.

It is noted that the order of the steps of this process of the invention may be interchangeable.

In some embodiments this process of the invention may further comprise, prior to the polymerization step (d), addition of a further amount of anaerobic degrading microorganisms (biomass) to the mixture obtained in step (c).

In some embodiments the further amount of anaerobic degrading microorganisms is provided in a dry form or in a combination of a dry form with wet form.

In some embodiments the polymeric support is polyurethane. In some further embodiments the pre-polymer is a hydrophilic polyurethane pre-polymer e.g., HYPOL*2002.

In some embodiments according to the processes of the invention the anaerobic degrading microorganisms (biomass) may be provided in a dry form (dry biomass) or in a combination of a dry form (dry biomass) with wet form (wet biomass). As used herein "dry biomass" refers to biomass with zero content of water. The term "wet biomass" is understood to refer to biomass that may comprise from above zero to about 99% of water e.g., 5%, 10%, 20%, 30%, 40%, 50%, 60%, 70%, 80% and 90% water content. In some embodiments the water content is 60%.

Without wishing to be bound by theory, the use of dry biomass in the processes of the invention may enable introduction of higher (relative to the amount in the wet form) amounts of biomass in the processes of the invention, e.g., in the preparation of the compositions, thus increasing the number of microorganisms in the compositions of the invention which may result in improved performance of the compositions of matter in the processes used according to the invention (e.g., improved biomass productions, reduction of adjustment period of the microorganisms to the conditions of the processes of the invention and as such reduction of start-up time periods of the processes according to the invention).

In some embodiments the dry biomass may be provide in a milled form for example by screening through 60 Mech (100 micrometer) or less. Such form may provide higher surface area of the biomass. In some further embodiments the dry biomass is provided in a form of a powder.

In some embodiments the polymerization in the processes of the invention may be initiated by the presence of water. In some embodiment the polymeric support and the water may be provided at a ratio of 1:1 up to 1:4, typically in a 1:1, 1:2, 1:3 and 1:4 ratio. In some embodiments the ratio is 1:1.5.

In yet further embodiments the polymerization may be initiated by the presence of a catalyst. In yet further embodiments the polymerization may be spontaneous. Yet in further embodiments the polymerization may occur at an ambient temperature.

In some embodiments the processes of the invention may optionally further comprise addition of a solution of humic acid to the reaction mixture. In some embodiments the humic acid solution is an aqueous solution. The humic acid may be added at any step of the processes. In some embodiments the humic acid may be added prior to the polymerization step. In such embodiments the humic acid is entrapped or embedded in the polymeric solid support. In some further embodiments the humic acid may be adsorbed onto the AC. In yet further embodiments the HA may be added following the polymerization step, to thereby obtain a composition of matter impregnated with humic acid.

In a further aspect of the present invention there is provided a process for the immobilization of the composition of matter according to the invention, the process comprises:
(a) providing anaerobic degrading microorganisms;
(b) mixing the anaerobic degrading microorganisms with particulate activated carbon;
(c) adding aqueous solution of humic acid to the mixture of step (b);
(d) adding a solid support to the resulting mixture of step (c); and
(e) collecting the resulting solid phase of step (d);
to thereby obtain a composition of matter comprising humic acid, particulate activated carbon and biomass immobilized on a solid support.

It is noted that the order of the steps of this process for the immobilization of the composition of matter according to the invention may be interchangeable.

In a further aspect of the present invention there is provided a process for the immobilization onto a solid support the composition of matter according to the invention, the process comprises:
(a) providing humic acid in aqueous solution;
(b) mixing the humic acid solution with particulate activated carbon;
(c) adding to the mixture resulting is step (b) anaerobic degrading microorganisms;
(d) contacting the mixture of step (c) with at least one monomer capable of being polymerized; and
(e) allowing polymerization of the at least one monomer to occur;
to thereby obtain a composition of matter comprising humic acid, particulate activated carbon and biomass immobilized on a solid support.

In some embodiments of this process of the invention, step (d) comprises contacting the mixture of step (c) with at least one first monomer comprising at least one first functional group and at least one second monomer comprising at least one second functional group, the first and second monomers are capable of being polymerized. It is noted that the order of the steps of this process for the immobilization of the composition of matter according to the invention may be interchangeable.

In a further aspect of the present invention there is provided a process for the immobilization onto a solid support a composition of matter comprising particulate activated carbon and biomass, the process comprises:
(a) providing anaerobic degrading microorganisms;
(b) mixing the anaerobic degrading microorganisms with particulate activated carbon;
(c) contacting the mixture of step (b) with at least one monomer capable of being polymerized;
(d) allowing polymerization of the at least one monomer to occur; and optionally
(e) adding aqueous solution of humic acid to the product of step (d);
to thereby obtain the composition of matter comprising particulate activated carbon and biomass immobilized on a solid support and optionally impregnated with humic acid.

In some embodiments of this process of the invention, step (c) comprises contacting the mixture of step (b) with at least one first monomer comprising at least one first functional group and at least one second monomer comprising at least one second functional group, the first and second monomers are capable of being polymerized.

It is noted that the order of the steps of this process for the immobilization of the composition of matter according to the invention may be interchangeable.

Yet, in a further aspect of the present invention there is provided a process for the immobilization onto a solid support a composition of matter comprising humic acid and particulate activated carbon, the process comprises:
(a) providing humic acid in aqueous solution;
(b) mixing the humic acid solution with particulate activated carbon;
(c) contacting the mixture of step (b) with at least one monomer capable of being polymerized;
(d) allowing polymerization of the at least one monomer to occur; and
(e) combining the solid phase resulting in step (d) with anaerobic degrading microorganisms;
to thereby obtain the composition of matter comprising humic acid and particulate activated carbon immobilized on a solid support and impregnated with anaerobic degrading microorganisms.

In some embodiments of this process of the invention step (c) comprises contacting the mixture of step (b) with at least one first monomer comprising at least one first functional group and at least one second monomer comprising at least one second functional group, the first and second monomers are capable of being polymerized.

It is noted that the order of the steps of this process for the immobilization of the composition of matter according to the invention may be interchangeable.

The term "monomer" as used herein above and below refers to a pre-polymer unit. "Polymeric building blocks" may be monomers, dimers, trimers, tetramers, or oligomers. Monomers may be identical or different. Polymerization of the pre-polymer units (monomers or building blocks) results in the formation of the polymer, which may be a homopolymer (where monomers are identical) or a co-polymer (where monomers are not identical). The terms "monomer" and "polymeric building block" may be used herein synonymously or interchanging.

In some embodiments pre-polymer unit may be soluble in aqueous and/or organic solution. Solubility may range from 0 to 100%. In some embodiments the pre-polymer unit may be provided in a form of oil.

In some embodiments of the processes of the invention the at least one first functional group is an isocyanate group (?N═C═O). In some embodiments, the at least one second functional group is an active hydrogen. Non limiting examples of active hydrogen are hydroxyl group, carboxylic group, amide group and amine group.

In some embodiments of the processes for the invention, the at least one first monomer comprises an isocyanate group and said at least one second monomer comprises hydroxyl group, and the first and second monomers are capable of being polymerized to produce polyurethane.

In some embodiments of the processes of the invention polymerization may be initiated by the presence of a catalyst such as $Ca^{+2}$, tertiary amines (such as dimethylcyclohexylamine), and organometallic compounds, (such as dibutyltin dilaurate and bismuth octanoate). In other embodiments polymerization is spontaneous. In some further embodiments polymerization may occur at ambient temperature for example at 20?C or 25?C. In yet further embodiments polymerization may be initiated by the presence of water.

In some embodiments of the processes according to the invention, the anaerobic degrading microorganisms may be provided in a dry form, wet form or a combination of the same.

The terms "waste", "sewage" and "contaminated matter" are interchangeable and as used herein above and below refer to effluents or other wastes comprising biomass amenable for anaerobic digestion. The waste may be in any form such as solid, semi-solid and liquid, such as water waste or wastewater. Non limiting examples of such waste or waste sources are industrial, agricultural, pharmaceutical, municipal, food, petroleum refineries, pulp, paper, plastic, dye, polymeric resins, animals, animal's excrement, olive mill wastewater, dairy waste, winery waste and so forth.

According to a further aspect of the present invention, there is provided a process for the manufacture of a composition of matter according to the invention, the process comprises:
(a) providing a sample of humic acid in aqueous solution;
(b) mixing the HA solution with particulate activated carbon;
(c) collecting the resulting solid phase e.g., by centrifugation; and
(d) combining the solid phase with anaerobic degrading microorganisms;
to thereby obtain a composition of matter comprising HA, PAC and anaerobic degrading microorganisms (biomass).

In some embodiments a base such as NaOH or KOH may be required to initially dissolve the HA in the aqueous solution as required in step (a).

In some further embodiments the pH of the aqueous solution in step (a) is adjusted to pH 7.0.

In some embodiments, the concentration of the humic acid in the above mentioned step (a) ranges between about 10 to about 12000 ppm. Exemplary concentrations of the humic acid are 10, 20, 25, 50, 100, 200, 350 and 500 ppm.

It is noted that the order of the steps of processes of the invention disclosed herein above and below may be interchangeable.

In a further aspect of the present invention there is provided a composition of matter as exemplified and described herein in the description and drawings.

Yet in a further aspect there is provided a composition of matter obtainable by the processes of the invention.

In accordance with an additional aspect of the present invention there is provided a process for the production of biogas from waste, the process comprises:
(a) providing a composition of matter according to the invention; and
(b) contacting the waste with the composition of matter under anaerobic conditions;
thereby producing the biogas.

In some embodiments this process of the invention may further comprise adjusting the pH of the solution resulting in step (b). In some embodiments the pH may be adjusted to pH 7.0.

In some further embodiments this process of the invention may be conducted at a temperature above room temperature such as 30?C and 37?C.

In some embodiments the waste may be provided in an aqueous solution. In other embodiments the waste may be provided in a glucose medium solution. Without wishing to be bound by theory, the glucose medium may be used as a control for the precise estimation of the biogas production.

In some embodiments the waste is selected from the group consisting of industrial waste, agricultural waste, pharmaceutical waste, municipal waste, food waste, petroleum refineries waste, olive mill wastewater, dairy waste and winery waste. In yet further embodiments the waste is a water waste or wastewater.

It is noted that for actual industrial implementation of this process of the invention of biogas production from waste, biogas production may be delayed until the adjustment of the microorganisms to the conditions of the process. Such an adaptation period may range from few days to few weeks. In some embodiments the adaptation period is one week. In some further embodiments the adaptation period is two weeks. In such embodiments when adaptation period is required, this process of the invention for biogas production may comprise a further step (c), the step comprises further addition of waste material to the mixture of step (b), e.g., reduction in adaptation time of the microorganisms in the processes for biogas production according to the invention.

As used herein the term "biogas" refers to a gas produced by the biological breakdown of organic matter in the absence of oxygen (anaerobic digestion of biodegradable materials). Non-limiting examples of biogas are methane, carbon dioxide, nitrogen, hydrogen, and carbon monoxide.

As used herein the term "anaerobic conditions" refers to conditions applied in the absence of oxygen due to the high organic load.

According to another aspect of the present invention, there is provided a use of a composition of matter according to the invention for the production of biogas from waste under anaerobic conditions.

According to a further aspect there is provided a composition of matter according to the invention for use in the production of biogas from waste under anaerobic conditions.

Yet according to another aspect there is provided a use of a composition of matter according to the invention for treating waste water.

Yet according to a further aspect there is provided a composition of matter according to the invention for treating waste water.

The compositions of matter according to the invention may be practiced with various types of bioreactors for biogas production known in the field, for example extended granular sludge system (EGSB), up-flow anaerobic sludge blanket system (UASB) or any type of bioreactor such as fixed bed bioreactor (also called anaerobic biofilters).

It should be noted that where various embodiments are described by using a given range, the range is given as such merely for convenience and brevity and should not be construed as an inflexible limitation on the scope of the invention. Accordingly, the description of a range should be considered to have specifically disclosed all the possible sub-ranges as well as individual numerical values within that range.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

It is noted that features of certain embodiments of the invention which are described in detail in the context of one aspect of the invention, may be applicable in other aspects of the invention.

DESCRIPTION OF NON-LIMITING EXAMPLES

Materials and Methods

The following ingredients were used in the examples described herein below.

HA is available from Sigma/Aldrich.

Activated carbon is available from Sigma/Aldrich (activated charcoal).

Oily/hydrophobic polyurethane (PU) monomers are available from Polytek Development Corp., PA (Poly 74-30 Clear B).

Hydrophilic polyurethane pre-polymers HYPOL*2000, HYPOL*2002, HYPOL* 3000, HYPOL*4000, HYPOL*5000 and HYPOL*5002 are available from Dow Chemical's (HYPOL*2002 catalog no. 126949, HYPOL*5002, catalog no. 229414). It is noted that such HYPL pre-polymers are available capped with aromatic isocyanates such as methylene diphenyl isocyanate (MDI) or toluene diisocyanates (TDI).

Sludge (biomass) is available from anaerobic extended granular sludge system (EGSB) treating paper mill wastewater and from UASB system treating the effluent of Prigat factory (Citrus juice industry, Israel).

Olive mill waste water characterization is provided in Table 1 by way of an example:

TABLE 1

Characterization of OMW

| Parameter | unit |
|---|---|
| pH | 4.85 |
| EC | 4.2 mS/cm$^2$ |
| BOD | 20000 mg/L |
| COD | 148360 mg/L |
| TSS | 38204 mg/L |
| VSS | 36768 mg/L |
| TS | 62688 mg/L |
| VS | 44690 mg/L |
| Total polyphenols | 2611 mg/L |
| TKN | 2394 mg/L |
| Ammonia | 934 mg/L |
| $PO_4^-$ as p | 285.8 mg/L |

Reference is now made to the following non-limiting examples, which together with the above illustrate the invention in a non-limiting fashion.

Example 1

Preparation of HA Adsorbed onto PAC

Various samples of HA were prepared as follows: 0.005-0.5 g of HA were dissolved in few drops of 0.1 N NaOH. Subsequently, water was added to reach a final concentration of HA of 25-12000 mg/L. The pH of the resulted solution was adjusted to 7.0 by HCl followed by addition of 3 g of powdered activated carbon (PAC). The suspension of 100 mL was shaken for 30 minutes followed by centrifugation. The solid was separated by decantation of the liquid phase.

Example 2

Biogas Production from Waste Material

HA-PAC obtained as in Example 1 was used in the production of biogas from olive mill wastewater under anaerobic condition as follows: 1 g of wet granulated sludge (biomass) from anaerobic extended granular sludge system (EGSB) treating paper mill wastewater was used.

0.05-1 gr of the HA-PAC were added to the sludge and gently mixed for several minutes. Subsequently, the mixture was added to olive mill wastewater (either 10 mL or 20 mL), diluted with water at a 1:1 ratio and optionally in the presence of glucose medium solution. The pH of the resulting mixture was adjusted to pH 7.0 (±0.1) and the mixture was placed in a 100 ml syringe and incubated at 37?C for 7-12 days. The biogas produced was monitored daily. At the end of the incubation period, the various samples were centrifuged and a liquid sample was taken from the supernatant for chemical oxygen demand, pH, polyphenols and volatile fatty acids (VFA) analysis.

The composition of the glucose medium used in the experiments is provided herein below by way of an example: 1.2 g/L $NH_4Cl$, 0.5 g/L yeast extract, 200 mg/L $MgSO_4.7H_2O$, 200 mg/L KCl, 25 mg/L $CaCl_2.2H_2O$, 40 mg/L $(NH_4)_2HPO_4$, 20 mg/L $FeCl_2.4H_2O$, 10 mg/L KI, 0.5 mg/L $MnCl_2.4H_2O$, 0.5 mg/L $CuCl_2.2H_2O$, 0.5 mg/L $ZCl_2$, 0.65 mg/L $Al_2(SO_4)_3$, 0.5 mg/L $NaMoO_4.2H_2O$, 0.5 mg/L $H_3BO_3$, 0.5 mg/L $NiCl_2.6H_2O$, 0.5 mg/L $Na_2SeO_3$.

FIG. 1 illustrates the enhancement effect of biogas production observed with the compositions of matter according to the invention. The figure shows the production of biogas from anaerobic degradation of olive mill wastewater using three different compositions of matter: sludge (free biomass), sludge with activated carbon and sludge with humic acid coated activated carbon. The figure indicates that the composition of matter comprising HA coated activated carbon offers an effective matrix for the anaerobic digestion of the organic content of the OMW. The biogas production match the reduction in COD as detailed in Table 1.

Without being bound by any theory, the presence of both HA and AC in the composition of matter according to the invention provides a synergistic effect of high adsorption capacity that leads to increased toxicity threshold of toxic materials and enhanced electrons shuttling between the electron donor (organic carbon) and the electrons acceptor (HA). This synergistic effect might lead to the better anaerobic digestion of effluents such as OMW.

It is noted that the production of biogas observed for the OMW sample with sludge only is slightly better than the one observed for the OMW with sludge and AC sample. Without wishing to be bound by theory, this may be a result of adsorption of organic matter by the AC, as such less organic matter is available for biogas production.

Figure 2A:
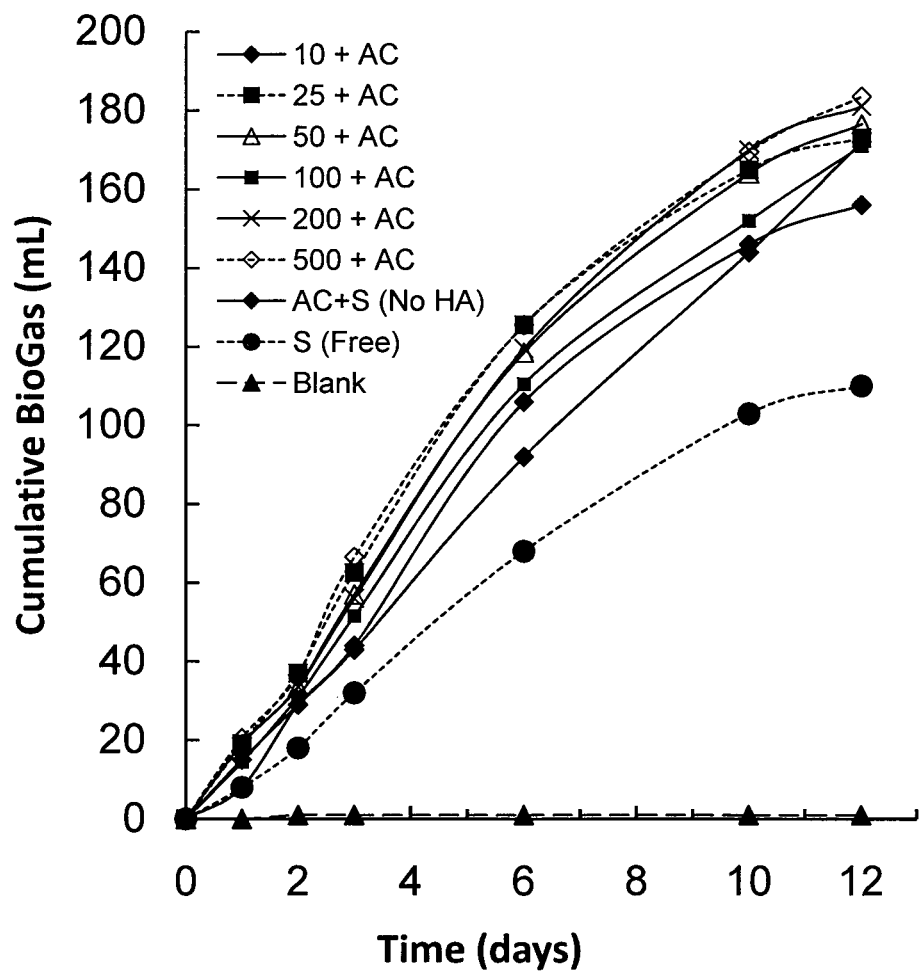
FIGS. 2A-2B show the biogas production profile observed with compositions of matter according to the invention at various concentrations of HA.

FIG. 2A illustrates the effect of humic acid concentrations (aqueous concentration in ppm prior to mixing with the activated carbon) on biogas production. It is noted that no major differences in biogas production were observed at the various HA concentrations. A slightly enhanced production was observed at the low concentration of 25 ppm. It is further noted that addition of HA to activated carbon provides with better performance compared to the free sludge (S) or to the free sludge with activated carbon (AC +S). Typically, the production of biogas was increased by 20-40% with composition of matter comprising humic acid coated activated carbon at the entire spectrum of HA concentration.

Example 3

Preparation of Compositions of Matter for Recycling Purposes

The samples used in FIG. 2A were re-used as follows: at the end of each biogas production experiment of each sample the OMW left was decanted and COD analyzed. The composition of matter was filtered on a small net and additional amount of OMW was added to each sample. A second run of biogas production experiment was conducted.

Figure 2B:
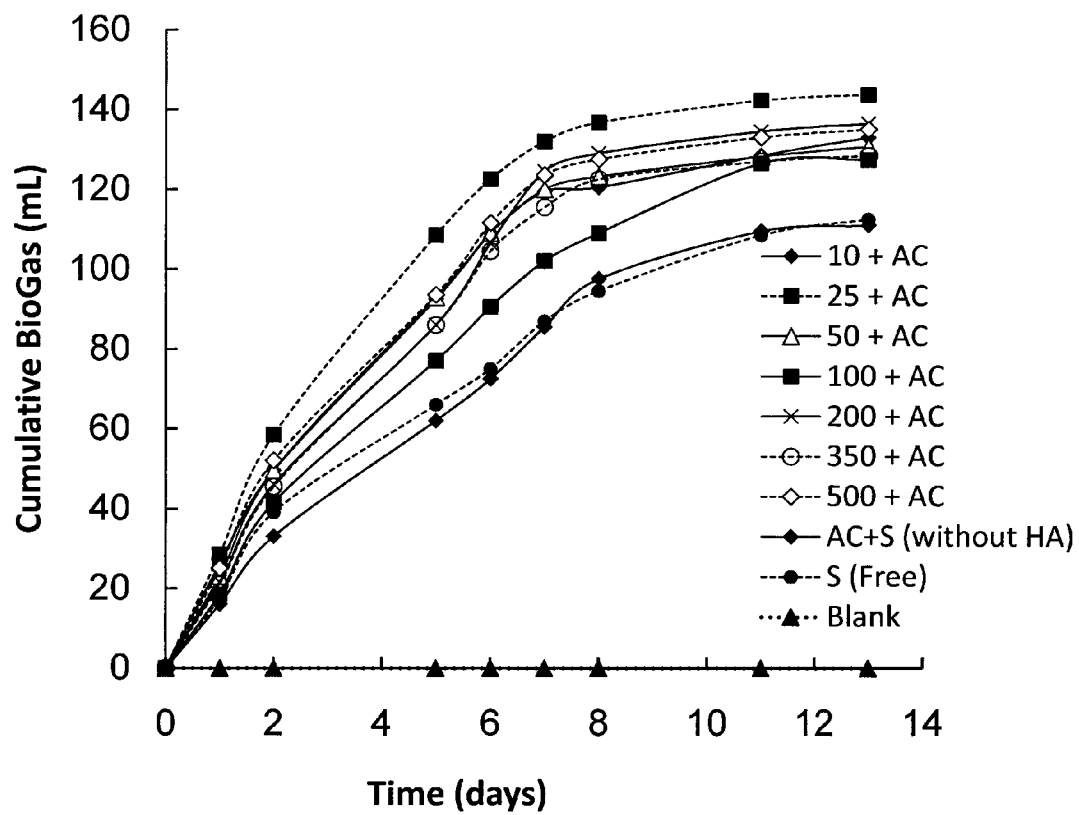

FIG. 2B illustrates the effect of humic acid concentration (aqueous concentration in ppm prior to mixing with activated carbon) on biogas production as observed with recycled/reused compositions of matter. It is noted that increase in the biogas production rate and quantity under the same experimental conditions was observed with recycled compositions of matter. Typically, an increase of 40-80% in the gas production in comparison with free biomass was observed with highest performance observed with the highest concentration of HA.

Example 4

The Effect of Buffered OMW Solution on Biogas Production

HA-PAC obtained as in Example 1 was used in the production of biogas from olive mill wastewater under anaerobic condition as follow:

$NaHCO_3$ was added to either 10 mL or 20 mL of OMW diluted with water at a 1:1 ratio to reach a final concentration of 4 g/L $NaHCO_3$.

1 g of wet granulated sludge (biomass) from anaerobic extended granular sludge system (EGSB) treating paper mill wastewater was used. 0.05-1 gr of the HA-PAC were added to the sludge and gently mixed for few minutes. Subsequently, the mixture was added to the OMW containing $NaHCO_3$. The pH of the resulting mixture was adjusted to pH 7.0 (±0.1) and the mixture was placed in a 100 ml syringe and incubated at 37?C for 7-12 days. The biogas produced was measured daily. At the end of the incubation period, the various samples were centrifuged and a liquid sample was taken from the supernatant for chemical oxygen demand, pH, polyphenols and volatile fatty acids (VFA) analysis.

Figure 3A:
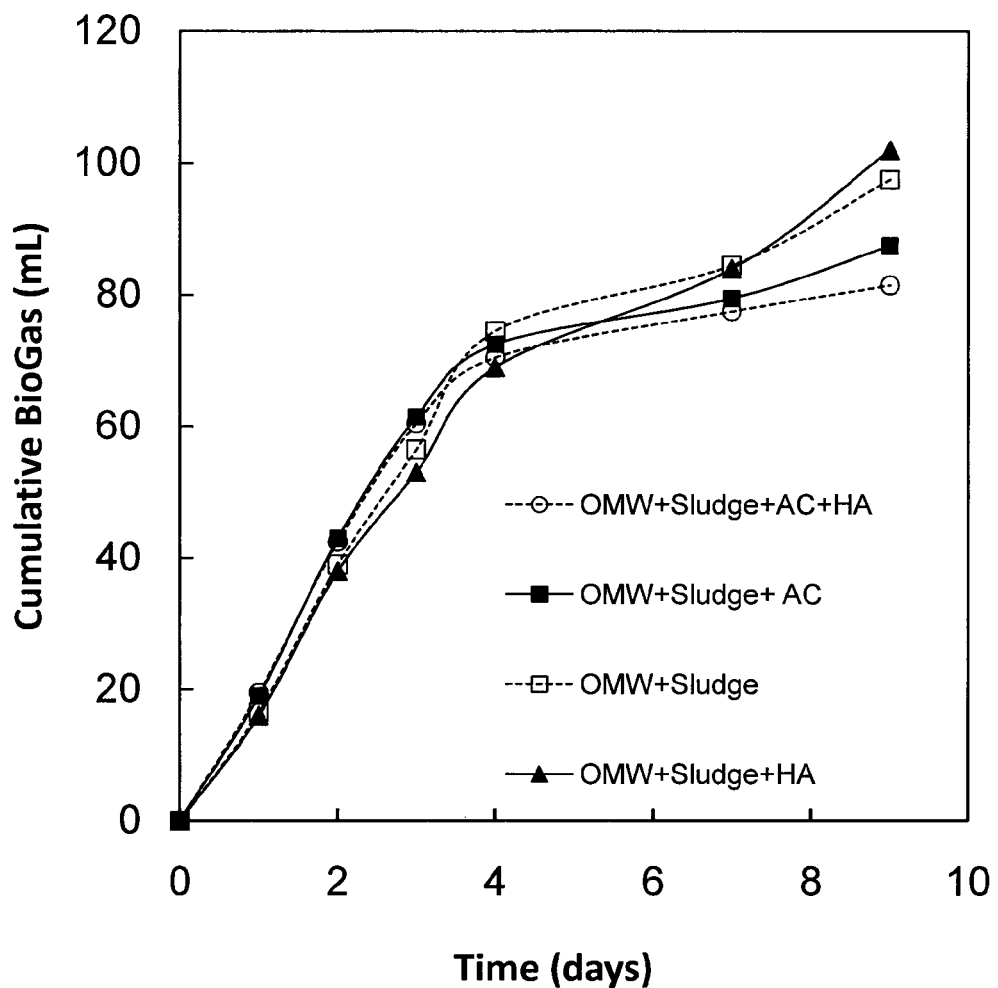
FIGS. 3A-3B show the effect of buffer on the biogas production.

FIG. 3A shows the biogas production observed for composition of matter prepared with buffered OMW. It is noted that no significant difference in the biogas production was observed for the various compositions of matter. Typically, similar biogas production profile was observed for samples of sludge and samples containing HA coated PAC compositions of matter with a slight advantage observed for the system with HA that may be attributed to the HA enhancement of the electron shuttling process.

Figure 3B:
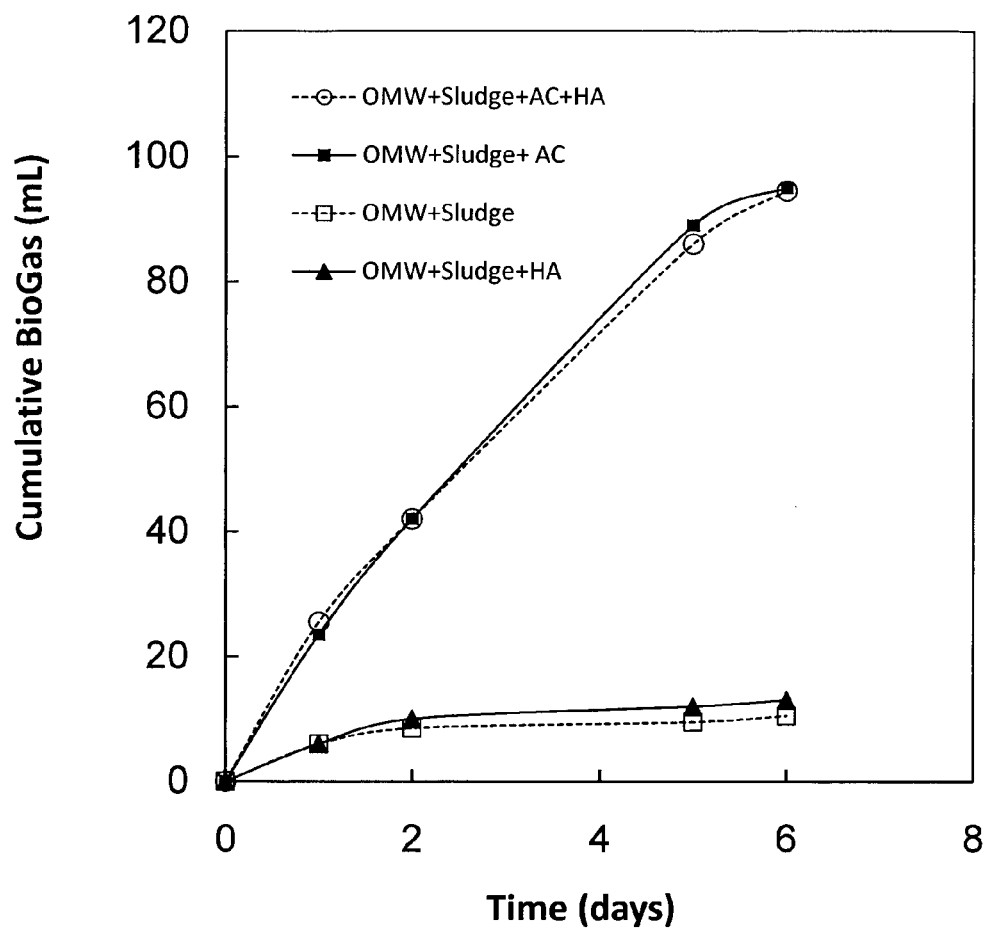

FIG. 3B shows the biogas production observed for composition of matter prepared with non-buffered OMW. The compositions of matter were prepared as described in Example 2. The figure illustrates the significant effect observed with the HA coated PAC compositions of matter.

Example 5

Immobilization of the Composition of Matter on a Solid Polymeric Support

A. Poly 74-30 Clear B Polymer

Sludge from the anaerobic digester (AD) of the wastewater of paper mill factory was mixed with sludge from Prigat factory (Citrus juice industry) at a 1:1 ratio. The water content of the sludge before drying was 90 ? 1%. Drying of the sludge was either at ambient air, by sun drying, by freeze drying, by vacuum followed by sun drying or by heating to temperature of up to 50?C. The draying process without applying heating conditions took about 2 to 3 days.

30 grams of wet biomass were added to half of the amount of AC specified for each sample in Table 2 and mixed until a homogeneous wet suspension was obtained. At the same time the second half portion of the amount of AC specified in Table 2 was mixed with 15 grams of dry biomass until a homogeneous mixture was obtained. The wet suspension was mixed with 15 grams of monomer A (oily PU monomer Poly 74-30 Clear B), the monomer possessing isocyante functional groups, followed by addition of the dry mixture and further mixing by a high shear mixer for 5 minutes. Subsequently, 15 grams of monomer B (oily PU monomer Poly 74-30 Clear B), the monomer possessing alcohol functional groups and further comprises a catalyst being capable of initiating the polymerization of monomers A and B, and the mixture was mixed for further 5 minutes. Polymerization was carried out at ambient conditions. The resulted mixture was poured on a plate and kept at room temperature until the polymerization was completed. The process proceeded for at least 24 hours and resulted in a solid product. The solid product was cut into different shapes such as cubes of 5×5×5 mm dimensions.

TABLE 2

Amount of various ingredients used in the preparation of the immobilized compositions of matter

| Sample | Monomer A (gr) | Monomer B (gr) | Wet Sludge (gr) | Dry sludge (gr) | AC (gr) |
|---|---|---|---|---|---|
| 1 | 15 | 15 | 30 | 15 | 0 |
| 2 | 15 | 15 | 30 | 15 | 0.3 |
| 3 | 15 | 15 | 30 | 15 | 1.5 |
| 4 | 15 | 15 | 30 | 15 | 3.0 |

Figure 4A:
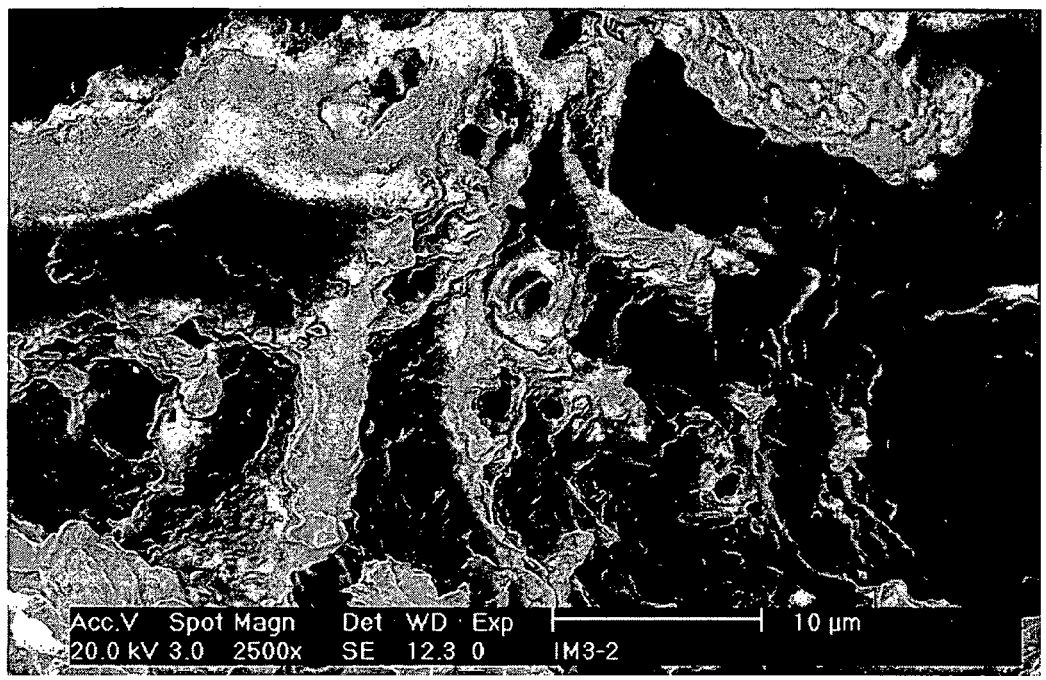
FIGS. 4A-4B show Scanning Electron Microscopic (SEM) images of various composition of matter according to the invention.

FIG. 4A shows a SEM image of a composition of matter obtained with Poly 74-30 Clear B polymer. The image clearly illustrates the porous nature of the composition.

B. HYPOL*2002 Pre-Polymer

Dry biomass: Sludge from the anaerobic system of the Prigat factory (Citrus juice industry) was dried to 0% water content either at ambient air, by sun drying, by freeze drying, by vacuum followed by sun drying or by heating to temperature of up to 50?C or 100 C. The dry sludge was milled and screened through 60 Mech (100 micrometer).

Wet Biomass: Wet biomass was collected from Prigat factory. The water content was reduced to 60% (free water) by the procedure disclosed herein above.

The Immobilization process: 15 grams of HYPOL*2002 Pre-polymer (Dow Chemical) were heated to 40° C. and added to a first beaker with 2.5 grams of dry sludge and 1 gram of powdered activated carbon. The mixture was mixed with a mechanical stirrer until homogenous mixture was obtained.

5 grams of dry biomass and 15 grams of wet biomass were added to a second baker containing 24 grams of water. The mixture was mixed at 10° C. with a mechanical stirrer until homogenous suspension was obtained.

The mixture of the first beaker was added to the mixture of the second beaker. The combined mixture was mixed by high shear mixer for 10-15 seconds.

The resulting mixture was poured on a plate and kept at room temperature until polymerization, which was initiated by the presence of water, was completed. The process proceeded for at least 15 minutes and resulted in a solid product. The solid product was cut into different shapes such as cubes of 5×5×5 mm dimensions or rectangular shape of 5×5×25 mm. The specific density of the resulted composition of matter was determined to be lower than 1 e.g., 0.9.

Figure 4B:
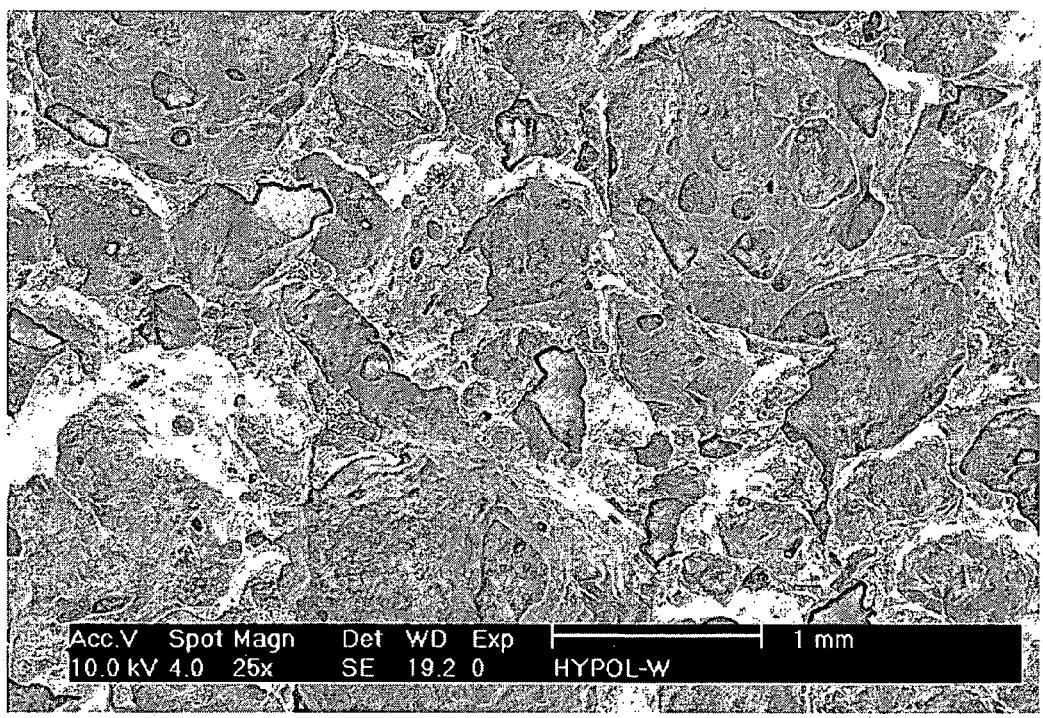

FIG. 4B shows a SEM image of a composition of matter obtained with HYPOL*2002 Pre-polymer. The image clearly illustrates the porous nature of the composition.

Figure 5:
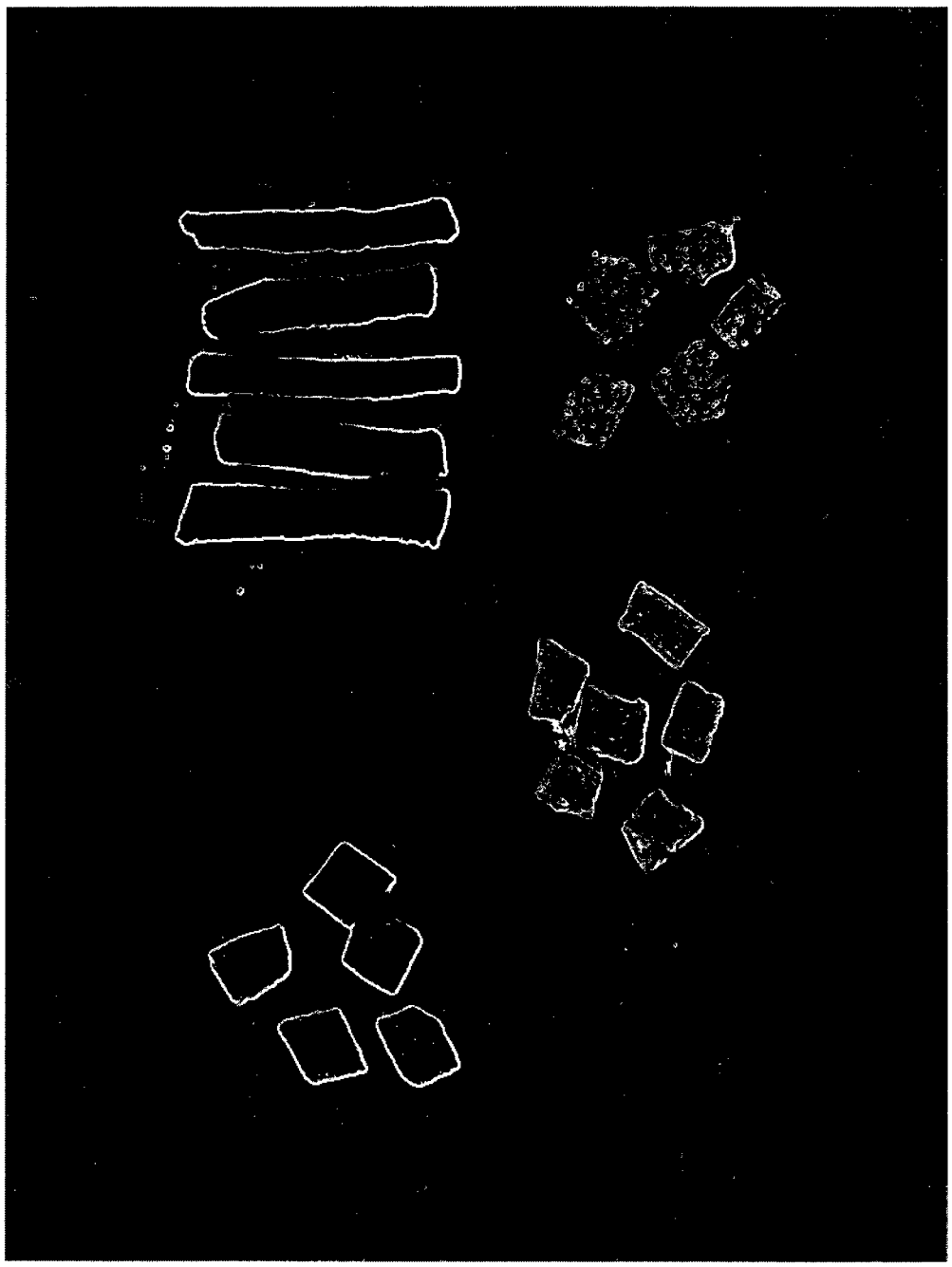
FIG. 5 shows a picture of various shapes of solid compositions of matter according to the invention.

FIG. 5 discloses pictures of compositions of matter obtained with the HYPOL*2002 Pre-polymer and cut into different shapes.

Example 6

Biogas Production Observed with Immobilized Compositions of Matter

The composition of matter of sample 4 in Table 2 was used in biogas production for about two weeks (a time period that may be required for the adaptation of the microorganisms to the specific conditions) followed by removal of the aqueous solution and addition of OMW. A second run of biogas production experiment was followed.

Figure 6A:
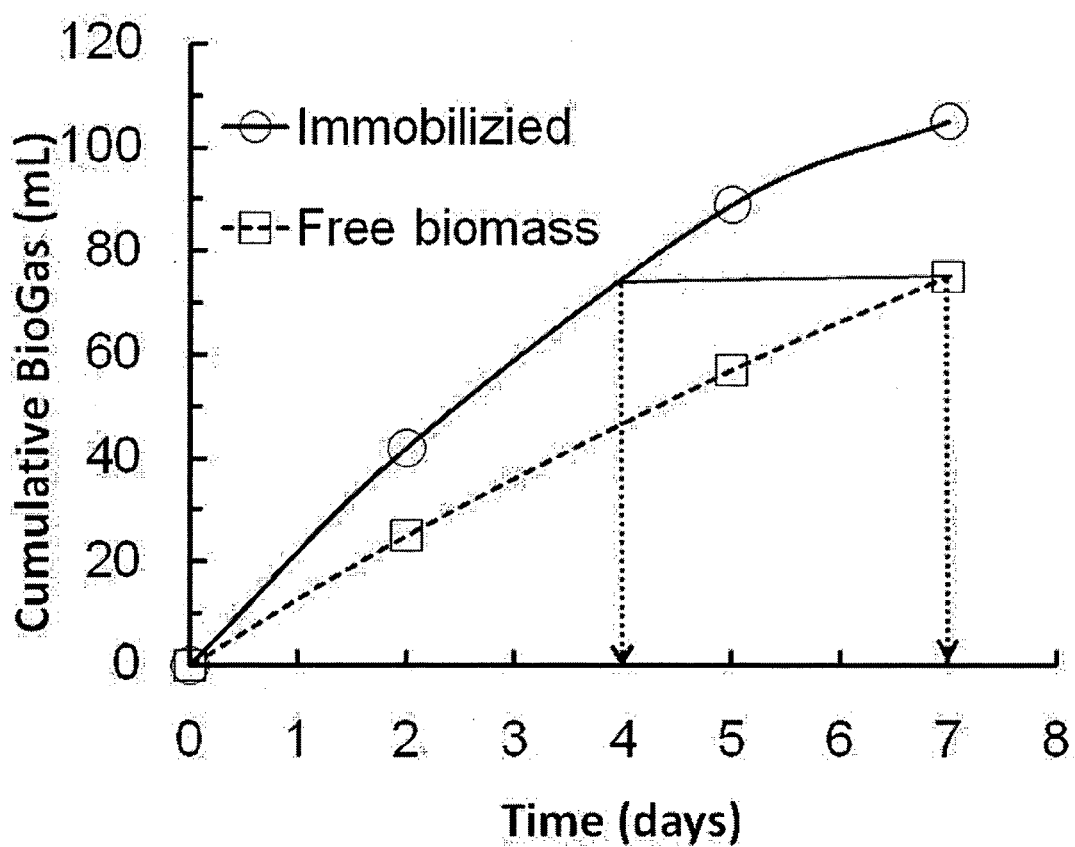
FIGS. 6A-6B shows the biogas production profile observed with various compositions of matter according to the invention.

FIG. 6A shows the biogas production observed with sample 4 of Table 2 at the second run and compared to the biogas production observed with free biomass (non-immobilized).

Figure 6B:
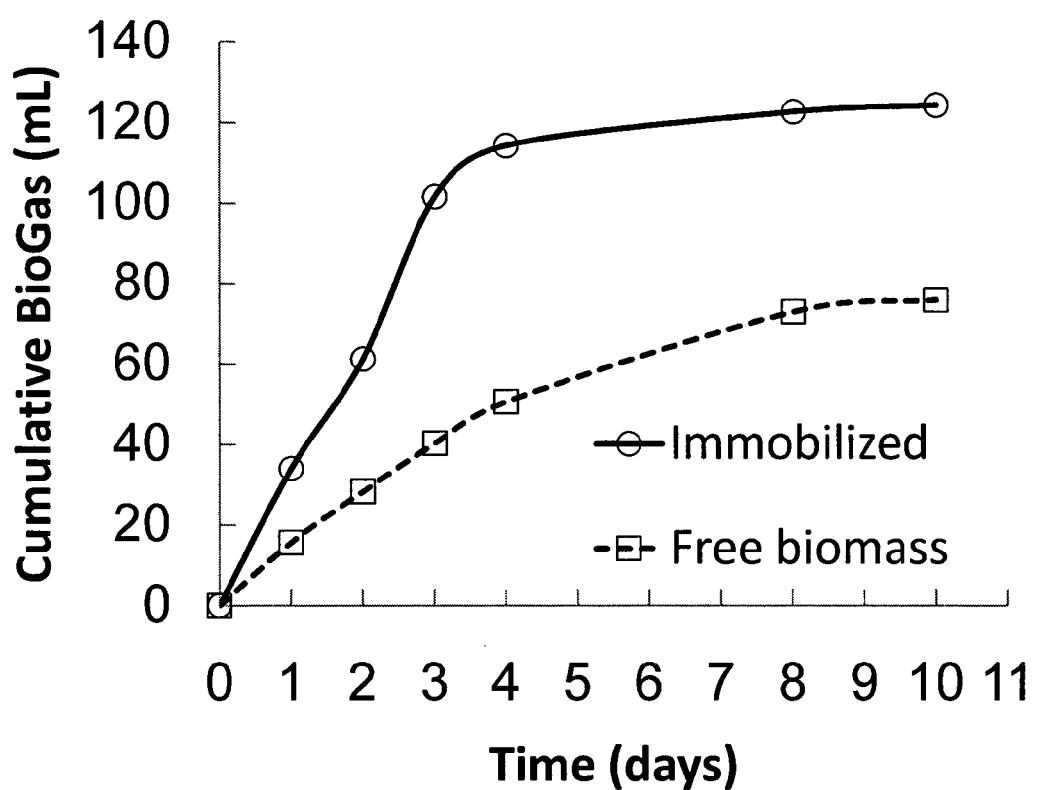

FIG. 6B shows the biogas production observed with the composition of matter obtained in Example 5B.

The significant effect of biogas production observed with the immobilized compositions of matter compared to the free biomass is clearly indicated in FIGS. 6A and 6B.

Example 7

Figure 7:
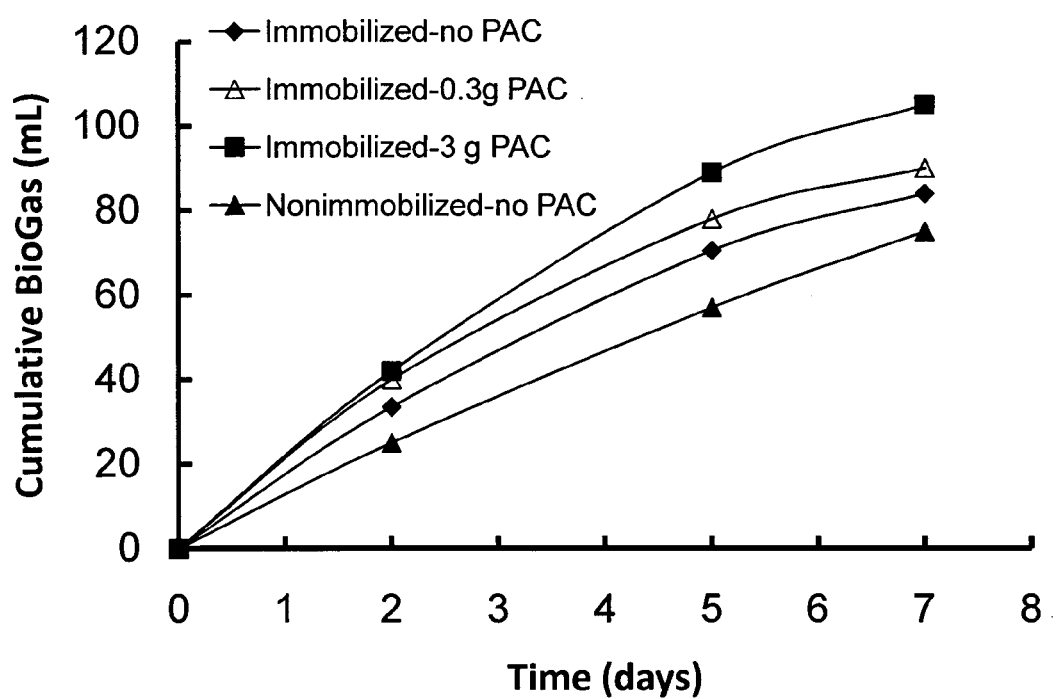
FIG. 7 shows the effect of PAC amount on the biogas production profile observed with various compositions of matter according to the invention.

The Effect of PAC on the Biogas Production as Observed with Immobilized Compositions of Matter FIG. 7 shows the biogas production observed with the immobilized compositions of matter as provided in Table 2 at different content of activated carbon (0, 0.3 and 3 g). It is noted that the biogas production is increased with increased AC content.

Example 8

The Effect of HA on the Biogas Production as Observed with Immobilized Compositions of Matter The compositions of matter prepared in Table 2 were placed in a 25 mg/L aqueous solution of HA for 2 hours.

Figure 8:
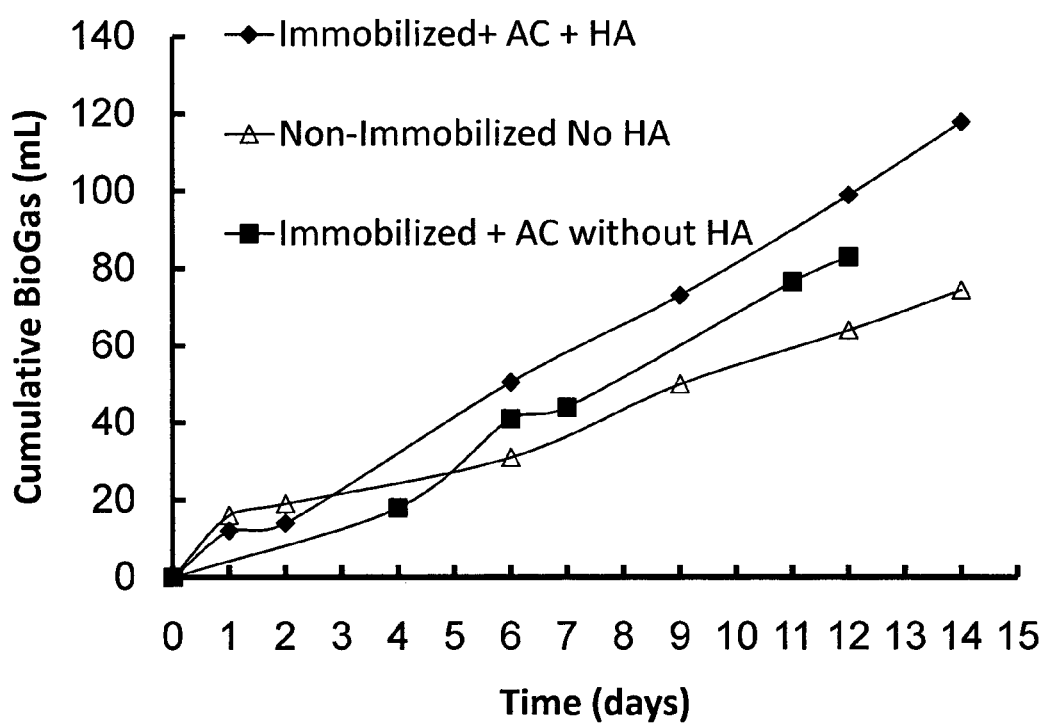
FIG. 8 shows the effect of HA on the biogas production profile observed with various compositions of matter according to the invention.

FIG. 8 shows the effect of the addition of HA on biogas production as observed with sample 4 of Table 2. It is noted that addition of 25 mg/L of HA to the solution increased the biogas production by 20%.

Example 9

The Use of Immobilized Compositions of Matter in Anaerobic Treatment Systems and their Effect of on the COD, TSS, BOD and Organic Loading The composition of matter obtained in Example 5B above was used in a pilot-scale anaerobic treatment system. The system was consisted of a continuous stirred tank reactor of an active volume of 50 liters (CSTR, a conditioning tank) and a cylindrical-shape reactor (bioreactor). The cylindrical-shape reactor of an active volume of 114 liters was filled with 50 kg of the composition of matter of Example 5B of rectangular shape (0.5×0.5×0.5 cm). In view of the low specific density of the composition of matter used (e.g., 0.9) a screener with 0.5 cm halls was set at the top of the cylindrical-shape reactor to prevent washout of the composition of matter from the bioreactor. The intrinsic floating capability provides an advantage in the use of such compositions as they are not accumulated at the bottom of the reactor and may be easily flown and distribute in the reactor. The reactor was equipped with a temperature sensor and a water heating system for temperature control. The temperature was set at 37° C.

Raw citrus wastewater from Prigat factory (Citrus juice industry) was pumped to the system directly from the wastewater-collecting tank of PriGat factory.

The influent flow rates used were 43.2 up to 172.8 L/day, corresponding to a hydraulic retention time (HRT) of 63 hr down to 16 h. The influent was fed to the CSTR and circulated into the cylindrical reactor. The inner flow rate of the circulation in the cylindrical reactor was 340 L/hr.

The system was operated and the amounts of the TSS, soluble COD, total COD and soluble BOD were detected over a period of time of 50 days. Over that period of time the influent had the following averaged values: $COD_{total}$ of 6700 mg/L, $COD_{soluble}$ of 5600 mg/L, $BOD_{soluble}$ of 3000 mg/L and TSS of 714 mg/L. The corresponding observed values of the effluent were 85% to 90% lower (it is noted that $COD_{soluble}$ and $BOD_{soluble}$ values refer to the values measured after filtration of the samples with glass fiber filter paper (GFA) used to remove the total suspended solids).

The significant reduction in the values of TSS, BOD and COD illustrates the advantageous of the compositions of matter used according to the invention. The compositions of matter according to the invention thus may be used in treatment of wastes such as agro-industrial wastewaters, inter-alia, assisting in prevention or reduction of the extent of system blockage associated with TSS in anaerobic treatment systems.

The invention claimed is:

1. A process for the manufacture of a composition of matter comprising a mixture of anaerobic degrading microorganisms, particulate activated carbon and a solid, polyurethane polymeric support, said process comprising:
    (a) providing a mixture of anaerobic degrading microorganisms, wherein said mixture of anaerobic degrading microorganisms comprises methanogenic bacteria, wherein said mixture of anaerobic degrading microorganisms is provided in a dry form or in a combination of a dry form with a wet form, wherein said wet form comprises up to 60% water;
    (b) mixing said mixture of anaerobic degrading microorganisms with a particulate activated carbon;
    (c) adding to said mixture obtained in step (b) at least one polyurethane pre-polymer capable of being polymerized to form a solid polymeric support; and
    (d) polymerizing said at least one polyurethane pre-polymer;
    thereby obtaining said composition of matter, wherein in said composition of matter said mixture of anaerobic degrading microorganisms and said particulate active carbon are entrapped in said solid, polyurethane polymeric support, and wherein said mixture of anaerobic degrading microorganisms constitutes 15% to 30% of the total weight of said composition of matter, and wherein said composition of matter is capable of producing biogas.

2. The process of claim 1, further comprising, prior to step (d), addition of a further amount of anaerobic degrading microorganisms to said mixture obtained in step (c), wherein said further amount of anaerobic degrading microorganisms is provided in a dry form or in a combination of a dry form with wet form.

3. The process of claim 1, wherein said polymerizing is initiated by addition of at least one of water and a catalyst.

4. The process of claim 1, wherein said polymerizing is spontaneous and/or occurs at ambient temperature.

5. The process of claim 1, wherein said methanogenic bacteria is selected from the group consisting of *Methanobacterium*, *Methanobacillus*, *Methanococcus*, and *Methanosarcina*.

6. The process of claim 1, wherein a weight ratio between said particulate activated carbon and the total weight of said composition of matter ranges from 0.01 to 0.04.

7. The process of claim 1, wherein said mixture of anaerobic degrading microorganisms constitutes 20% to 30% of the total weight of said composition of matter.

8. The process of claim 1, wherein said biogas is methane.

9. The process of claim 1, wherein said polyurethane pre-polymer is a hydrophilic polyurethane pre-polymer.

10. The process of claim 1, wherein said polyurethane pre-polymer is a hydrophobic polyurethane pre-polymer.

* * * * *